(12) United States Patent
Liimatainen et al.

(10) Patent No.: US 7,932,719 B2
(45) Date of Patent: Apr. 26, 2011

(54) MAGNETIC RESONANCE CONTRAST USING FICTITIOUS FIELD RELAXATION

(75) Inventors: Timo Liimatainen, Kuopio (FI); Michael G. Garwood, Medina, MN (US); Dennis J. Sorce, Cockeysville, MD (US); Shalom Michaeli, St. Paul, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 0 days.

(21) Appl. No.: 12/731,936

(22) Filed: Mar. 25, 2010

(65) Prior Publication Data

US 2010/0237866 A1 Sep. 23, 2010

Related U.S. Application Data

(63) Continuation of application No. PCT/US2008/011103, filed on Sep. 25, 2008.

(60) Provisional application No. 60/995,193, filed on Sep. 25, 2007.

(51) Int. Cl.
*G01V 3/00* (2006.01)
(52) U.S. Cl. ........................................ 324/307; 324/309
(58) Field of Classification Search .......... 324/300–322; 600/407–445
See application file for complete search history.

(56) References Cited

U.S. PATENT DOCUMENTS

| | | | |
|---|---|---|---|
| 4,820,983 A | 4/1989 | Bendall et al. | |
| 6,219,571 B1 | 4/2001 | Hargreaves et al. | |
| 6,448,769 B1 * | 9/2002 | Rosenfeld et al. | 324/307 |
| 6,750,649 B1 * | 6/2004 | Rosenfeld | 324/307 |
| 7,230,424 B1 * | 6/2007 | Morrone | 324/309 |
| 7,279,899 B2 * | 10/2007 | Michaeli et al. | 324/318 |
| 2006/0244447 A1 * | 11/2006 | Michaeli et al. | 324/309 |
| 2007/0040553 A1 | 2/2007 | Hajimiri et al. | |

FOREIGN PATENT DOCUMENTS

WO WO 2009042168 A2 4/2009
WO WO-2009042168 A3 4/2009

OTHER PUBLICATIONS

"International Application Serial No. PCT/US2008/011103, Search Report mailed May 26, 2009".
"International Application Serial No. PCT/US2008/011103, Written Opinion mailed May 26, 2009".
Garwood, Michael, "Advances in Magnetic resonance", *Journal of Magnetic Resonance 153*, (2001), 155-177.
Michaeli, Shalom, et al., "Assessment of Brain Iron and Neuronal Integrity in Patients with Parkinson's Disease Using Novel MRI Contrasts", *Movement Disorders*, vol. 22., (Nov. 3, 2007), 334-340.

* cited by examiner

*Primary Examiner* — Brij B Shrivastav
(74) *Attorney, Agent, or Firm* — Schwegman, Lundberg & Woessner P.A.

(57) ABSTRACT

A system includes a signal generator and a processor. The signal generator is configured to couple with a magnetic resonance transmitter coil. The processor is configured to execute instructions to control the signal generator. The instructions include forming a sequence of waveforms. The sequence is configured to generate spin relaxation in a fictitious field in a third rotating frame of reference based on at least one magnetic field component that arises based on an effective field in a second rotating frame of reference. The third rotating frame of reference is of a higher order than the second rotating frame of reference and the second rotating frame of reference is of a higher order than the first rotating frame of reference.

27 Claims, 10 Drawing Sheets
(4 of 10 Drawing Sheet(s) Filed in Color)

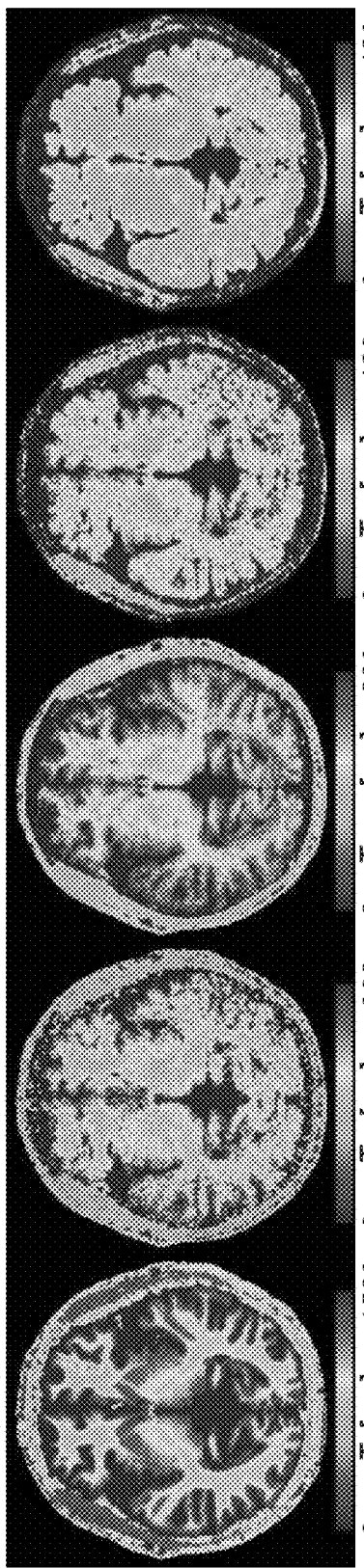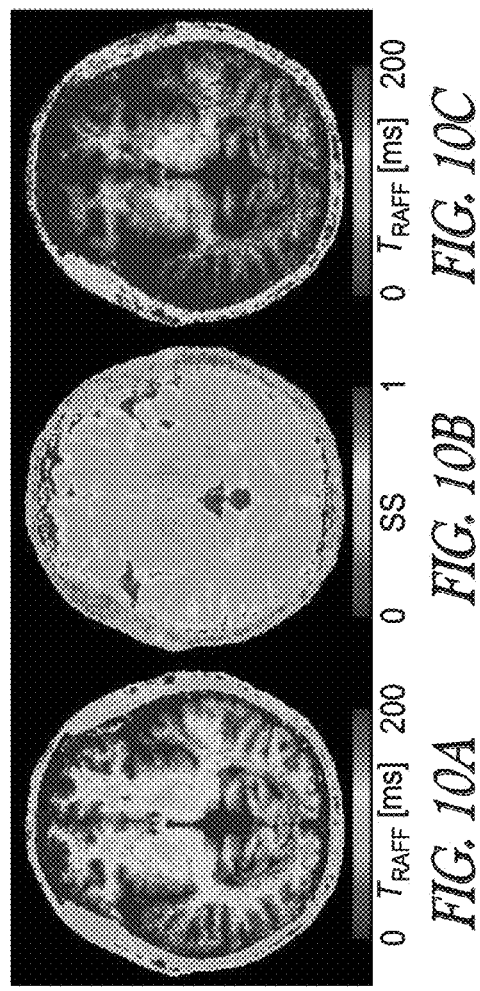

MAGNETIC RESONANCE CONTRAST USING FICTITIOUS FIELD RELAXATION

CLAIM OF PRIORITY

This application is a continuation under 35 U.S.C. 111(a) of International Application No. PCT/US2008/011103 filed Sep. 25, 2008 and published in English as WO 2009/042168 on Apr. 2, 2009, which claims benefit of priority, under 35 U.S.C. Section 119(e), to Liimatainen et al., U.S. Provisional Patent Application Ser. No. 60/995,193, entitled "MAGNETIC RESONANCE CONTRAST USING FICTITIOUS FIELD RELAXATION," filed on Sep. 25, 2007, which applications are incorporated herein by reference.

STATEMENT REGARDING FEDERALLY SPONSORED RESEARCH OR DEVELOPMENT

This invention was made with government support under NIH P30 NS057091 and under award number BTRR P41 RR008079, both from the National Institutes of Health. The government has certain rights in this invention.

BACKGROUND

There is interest in using ultra-high magnetic fields for magnetic resonance. High magnetic field strength leads to improved signal to noise ratio (SNR). However, increased magnetic field strength also can lead to undesirable heating of the region of interest.

OVERVIEW

A system includes a signal generator and a processor. The signal generator is configured to couple with a magnetic resonance transmitter coil. The processor is configured to execute instructions to control the signal generator. The instructions include forming a sequence of waveforms. The sequence is configured to generate spin relaxation in a fictitious field in a third rotating frame of reference based on at least one magnetic field component that arises based on an effective field in a second rotating frame of reference. The third rotating frame of reference is of a higher order than the second rotating frame of reference and the second rotating frame of reference is of a higher order than the first rotating frame of reference.

In one example, the processor is configured to modulate the effective field. In one example, the processor is configured to maintain the effective field at a constant value. In one example, the fictitious field includes a swept frequency. In one example, the fictitious field arises under sub-adiabatic conditions. In one example, the fictitious field includes an axis of quantization of the third rotating frame of reference.

In one example, the system includes a receiving coil and an output device. The receiving coil is configured to detect the relaxation in the fictitious field. The output device is coupled to the receiving coil and is configured to render human perceivable data.

One example includes a method. The method includes directing a plurality of waveforms to a region of interest. The plurality of waveforms are configured to produce a fictitious field vector. The method includes generating data based on a magnetic resonance signal received from the region. The data corresponds to relaxation of magnetization in a third rotating frame and is based on relaxation arising in a second rotating frame. The fictitious field vector arises in the third rotating frame. The third rotating frame has a Z-axis collinear with the fictitious field vector. The Z-axis of the second rotating frame is collinear with $\omega_{eff}$ and $\omega_{eff}$ is a vector based on a frequency offset and based on an amplitude of a pulse of the plurality of waveforms.

In one example, the plurality of waveforms is configured to modulate the fictitious field vector as a function of time. In one example, the relaxation of magnetization in the second rotating frame is based on a combination of longitudinal rotating frame relaxation and transverse rotating frame relaxation of the second rotating frame. In one example, directing the plurality of waveforms includes sequentially applying a first pulse train and an excitation pulse. In one example, the first pulse train is applied before the excitation pulse. In one example, the first pulse train is applied after the excitation pulse. In one example, directing the plurality of waveforms includes applying a pulse having sine and cosine functions with equal amplitude. In one example, $\omega_{eff}$ is a vector sum of a frequency offset and an amplitude. In one example, rotation of the magnetization from the Z-axis of the second rotating frame to an X-Y plane of the second rotating frame causes the magnetization to precess about a cone having an angle relative to the fictitious field of approximately 45 degrees during the pulse. In one example, directing the plurality of waveforms includes applying a waveform having a plurality of lobes where each lobe has a first segment and a second segment. The first segment includes a sine amplitude modulation function and cosine frequency modulation function and the second segment includes a backward first segment. In one example, the first segment has phase zero and the second segment has phase 180 degrees. In one example, the plurality of waveforms includes a sequence of four segments including a first segment having sine amplitude modulation and cosine frequency modulation, a second segment includes amplitude and phase of the first segment driven backwards and a 180 degree shifted phase and a third segment includes a 180 degree shifted phase of the first segment and a fourth segment includes a 180 degree shifted phase of the second segment. In one example, the relaxation rate of magnetization of dipolar origin during a duration of the pulse is slower than the relaxation in the first rotating frame. In one example, the pulse causes refocusing of magnetization. In one example, the relaxation includes a combination of transverse relaxation in the third rotating frame and of longitudinal relaxation in the third rotating frame. In one example, relaxation includes transverse relaxation orthogonal to the fictitious field in the third rotating frame. In one example, generating data includes fitting measured signal intensity decay to an exponential function. In one example, fitting measured signal intensity decay to the exponential function includes fitting to function having a plurality of exponentials. In one example, generating data includes establishing a steady state.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views Like numerals having different letter suffixes may represent different instances of similar components. The draw

FIGS. 9A-9E illustrate representative relaxation maps from human brain obtained using $T_1$, adiabatic $T_{1\rho}$, RAFF, adiabatic $T_{2\rho}$, and $T_2$ relaxation mapping techniques.

FIGS. 10A-10C illustrate a map of the time constant describing relaxation along a fictitious field ($T_{RAFF}$), a map of the fractional steady state obtained from the same fitting and then normalized by the initial signal intensity, and a map of $T_{RAFF}$ generated using only a single mono-exponential function.

DETAILED DESCRIPTION

Figure 1:
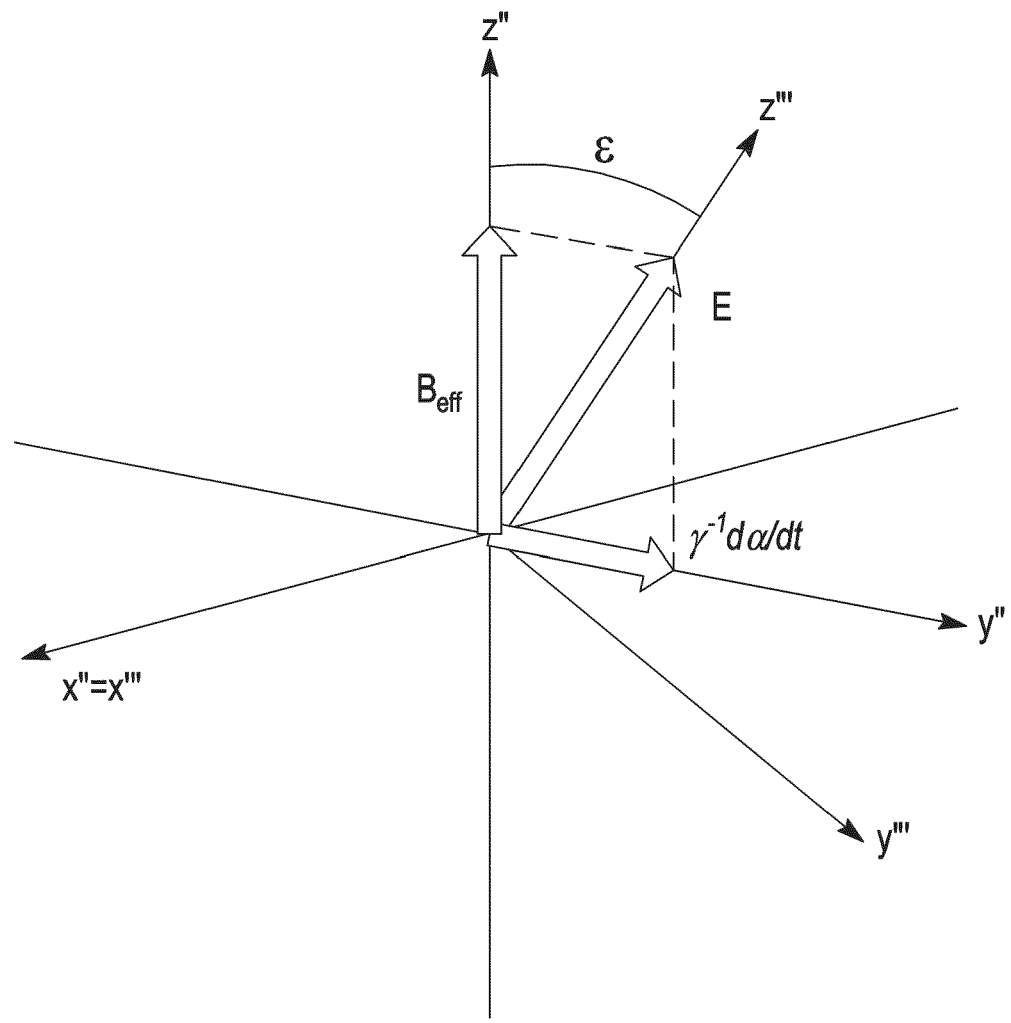
- FIG. 1 illustrates a coordinate system used for describing the fictitious E-frame of reference.

A method to measure rotating frame relaxation and to create contrast for MRI is disclosed. Relaxation along a fictitious field (RAFF) generated by amplitude-modulated and frequency-modulated irradiation in a sub-adiabatic condition. RAFF is demonstrated using a radio frequency pulse based on sine and cosine modulations of equal amplitude, which gives rise to a stationary fictitious magnetic field E in a doubly rotating frame of reference (the E-frame). Under these conditions, dipolar relaxation theory predicts the rotating frame relaxation time constant ($T_{RAFF}$) to be unique and the longitudinal and transverse components ($T_{1\rho,E}$ and $T_{2\rho,E}$, respectively) to be equal.

Experimental measurements on three different solutions (Gd-DTPA solution, ethanol and water mixture, and acetate dissolved in glycerol/water) support the theoretical predictions. The value of $T_{RAFF}$ is generally insensitive to the initial orientation of the magnetization vector. Relaxation mapping experiments in human brain at 4T indicate the ability to create MRI contrast based on RAFF. Contrast-to-noise ratios between several different brain regions differ as a consequence of $T_{RAFF}$ being distinct from the laboratory frame relaxation times ($T_1$ and $T_2$) and adiabatic rotating frame relaxation times ($T_{1\rho}$ and $T_{2\rho}$) in these tissues. In addition, as compared with adiabatic $T_{1\rho}$ and $T_{2\rho}$ pulse trains of equal durations, RAFF required less radio frequency power deposition and therefore can be more readily used for rotating frame relaxation studies in humans.

Part 1

As magnet technology has continued to advance, the field strength ($B_0$) used for NMR has increased. This trend has been fueled in part by the quest for increased signal-to-noise ratio (SNR). On the other hand, as $B_0$ increases, the laboratory frame (LF) longitudinal relaxation time ($T_1$) becomes less sensitive to slow molecular motions because $T_1$ is dominated by dipolar fluctuations occurring mainly near the Larmor frequency, a $\omega_0 = \gamma B_0$, where $\gamma$ is the magnetogyric ratio. Reduced sensitivity to slow molecular motions is particularly relevant to the field of biomedical magnetic resonance imaging (MRI), since tissue-specific differences in $T_1$ are relied upon for image contrast (i.e., $T_1$-weighting). Relaxation in the presence of radio frequency (RF) irradiation, i.e., the rotating frame longitudinal and transverse relaxation times ($T_{1\rho}$ and $T_{2\rho}$, respectively), can provide information about slow molecular motions at any field strength. Although $T_{1\rho}$ and $T_{2\rho}$ measurements can be performed with time-invariant RF pulses, these measurements can also be performed with pulses utilizing amplitude (AM) and frequency-modulated (FM) functions under conditions which accomplish an adiabatic full-passage (AFP). Rotating frame relaxation times can be more informative than $T_1$ and $T_2$ in assessing specific tissue properties and in detecting certain pathologic changes. For example, as to patients with Parkinson's disease, adiabatic $T_{2\rho}$ can be more sensitive than $T_2$ to pathological changes occurring in the brain.

Potential considerations for making rotating frame relaxation measurements in living systems is the RF power (i.e., specific absorption rate (SAR)) and tissue heating. In some cases, low RF power is used to measure $T_{1\rho}$ with the classical spin-lock experiment. For example, $T_{1\rho}$ measured with low spin-lock power ($B_1 = 2.0 \cdot 10^{-6}$ T) can provide an imaging marker to detect gene therapy response in a rodent glioma model. The RF power for spin-locking may limit the application of classical $T_{1\rho}$ experiments in studies of humans at high magnetic fields.

To avoid power constraints, the off-resonance $T_{1\rho}$ experiment can be used. However, utilization of the off-resonance $T_{1\rho}$ method for MRI is limited due to several technical obstacles, such as sensitivity to $B_1$ and $B_0$ imperfections, which are often difficult to avoid. Also, in some cases, high RF power deposition is used to fulfill the adiabatic condition for adiabatic $T_{1\rho}$ and $T_{2\rho}$ measurements.

The present subject matter includes a method to create and exploit a "fictitious" magnetic field for rotating frame relaxation studies. The fictitious field is created by a rapid, sub-adiabatic modulation of the RF amplitude and frequency. The method is called RAFF (relaxation along a fictitious field). Employing second order perturbation theory, RAFF provides sensitivity to detect changes in rotational correlation time, $\tau_c$. RAFF can assess molecular dynamics and generate contrast for MRI while using less RF power than that typically used for $T_{1\rho}$ and $T_{2\rho}$ measurements.

Part 2

An understanding of $T_{1\rho}$ and $T_{2\rho}$ methods utilizing FM pulses can be facilitated by analyzing the magnetic field components and motion of M in two different rotating coordinate frames. The first frame rotates in synchrony with the time-dependent pulse frequency ($\omega_{RF}(t)$), and is thus known as the $\omega_{RF}$-frame with axis labels x', y', and z'. In the $\omega_{RF}$-frame, during an AFP pulse the orientation of $B_1$ is fixed (by convention, $B_1$ is along the x'-axis). The effective field ($B_{eff}(t)$), which sweeps from +z' to −z' (or vice versa), is given by $$B_{eff}(t) = \sqrt{B_1^2(t) + (\Delta\omega(t)/\gamma)^2}, \quad (1)$$

where $\Delta\omega(t)$ is the time-dependent offset frequency given by, $$\Delta\omega(t) = \omega_0 - \omega_{RF}(t). \tag{2}$$

The AM and FM functions of an AFP pulse produce a sweep of $B_{eff}(t)$, with a tilt angle relative to the z' axis given by $$\alpha(t) = \tan^{-1}\left(\frac{\omega_1(t)}{\Delta\omega(t)}\right), \tag{3}$$

where $$\omega_1(t) = \gamma B_1(t). \tag{4}$$

Because $B_{eff}$ is time-dependent, adiabatic rotating frame relaxation time constants are also time-dependent ($T_{1\rho}(t)$ and $T_{2\rho}(t)$). At any given time point during the pulse, the relaxation rate will depend on the orientation and amplitude of $B_{eff}(t)$, as well as the orientation of M relative to $B_{eff}(t)$ at that particular moment in time. When the adiabatic condition is satisfied throughout an AFP pulse, the component of M that is initially aligned with $B_{eff}$ will remain approximately aligned (or "locked") with $B_{eff}(t)$ throughout the pulse; accordingly, this magnetization experiences time-dependent $T_{1\rho}$ relaxation. In this manner, $T_{1\rho}$ contrast can be produced in MRI by transmitting a windowless train of AFP pulses prior to the excitation pulse Likewise, if M is placed perpendicular to $B_{eff}$ at t=0, M will evolve with the effective frequency $\omega_{eff}(t) = \gamma B_{eff}(t)$ and will lie close to the plane perpendicular to $B_{eff}(t)$ at all times during the AFP pulse. Hence, by first creating transverse magnetization ($M_{xy}$) and subsequently transmitting a windowless train of AFP pulses, $T_{2\rho}$ contrast can be generated.

The description above applies to the situation in which the adiabatic condition, $B_{eff}(t) \gg |\gamma^{-1} d\alpha/dt|$, is fulfilled throughout the pulse.

In the RAFF method the adiabatic condition is violated by choosing the modulation functions to satisfy the condition $B_{eff}(t) = |\gamma^{-1} d\alpha/dt|$. To facilitate an understanding of RAFF, the vector analysis moves to a second frame of reference which is a doubly rotating frame known as the $\omega_{eff}$-frame, with axis labels x", y", and z", as shown in FIG. 1. In the $\omega_{eff}$-frame, by definition, the orientation of $B_{eff}$ remains fixed along the z" axis. Initially (t=0), the $\omega_{RF}$-frame and $\omega_{eff}$-frame are superimposed (i.e., z"=z'), and at later times, the two frames are related by the $B_{eff}$ rotation which took place in the $\omega_{eff}$-frame around y'(=y"). This rotation in the $\omega_{RF}$-frame (i.e., $\alpha(t)$) gives rise to a fictitious field in the $\omega_{eff}$-frame, and the effective field vector E(t) in the $\alpha_{eff}$-frame is thus the vector sum of $B_{eff}(t)\hat{z}"$ and this fictitious field, $[\gamma^{-1} d\alpha/dt]\hat{y}"$. As such, the magnitude of E is given by $$E(t) = \sqrt{B_{eff}^2(t) + \left(\gamma^{-1}\frac{d\alpha}{dt}\right)^2}. \tag{5}$$

The angle between E and $B_{eff}$ is defined as, $$\varepsilon(t) = \tan^{-1}\left(\frac{\gamma B_{eff}(t)}{d\alpha/dt}\right). \tag{6}$$

When $B_{eff}(t) = |\gamma^{-1} d\alpha/dt|$, a stationary E exists in the $\omega_{eff}$-frame at an angle $\epsilon = \pi/4$ relative to the z" axis. This E field is utilized in the RAFF method and is associated (or collinear) with the z'" axis of the third rotating frame of reference having axes defined as x'", y'", z'". The E field can be used to excite magnetization and in rotating frame relaxation experiments.

To satisfy the condition $B_{eff}(t) = |\gamma^{-1} d\alpha/dt|$, the AM and FM functions of the RAFF pulse are constructed from sine and cosine functions (SC) with equal amplitudes. Accordingly, during the pulse time t, the AM and FM functions are given by, $$\omega_1(t) = |\omega_1^{max} \sin(\omega_1^{max} t)| \text{ for } t = [0, T_p] \tag{7}$$

and $$\Delta\omega(t) = \omega_1^{max} \cos(\omega_1^{max} t) \text{ for } t = [0, T_p], \tag{8}$$

respectively, where $T_p$ is the pulse length in seconds, $\omega_1^{max}$ is the maximum value of the AM function, and in the specific case of RAFF, $\omega_1^{max}$ is also the maximum value of the frequency offset function, in radians/second. With this pulse, the frequency function (Eq. (8)) sweeps from its initial value ($\Delta\omega = \omega_1^{max}$) toward the resonance condition ($\Delta\omega = 0$) and beyond ($\Delta\omega < 0$), while the pulse amplitude (Eq. (7)) varies in a sinusoidal manner The argument of both modulation functions must be the same ($\omega_1^{max} t$) to create the condition $\epsilon = \pi/4$. In the condition $\epsilon = \pi/4$, the magnitude of the effective field remains constant and is given by $$E = \sqrt{\sqrt{2}}\omega_1^{max}.$$

Hence, with a given setting of $\omega_1^{max}$, the effective field is larger with RAFF as compared with on-resonance $T_{1\rho}$ spin-lock ($E > \omega_1^{max}$).

FIG. 1 illustrates a coordinate system used for describing the fictitious E-frame of reference. Effective field $B_{eff}$ (grey arrow) undergoes rotation with frequency $\omega_0 + \omega_{RF}$ relatively to the laboratory frame. The rotation of $B_{eff}$ in the y'z' plane leads to the fictitious field component $\gamma^{-1} d\alpha/dt$ along the y"-axis in the $\omega_{RF}$-frame. The $B_{eff}$ is aligned along $\pm z$"-axis in the $\omega_{eff}$-frame and the fictitious field E is the vector sum of $B_{eff}$ and $d\alpha/dt$. The angle $\epsilon$ between $\omega_{eff}$ and E depends on the $\omega_{eff}$ and the $d\alpha/dt$, and it is equal to $\pi/4$ with condition $d\alpha/dt = \omega_{eff}$. In the E-frame, E-field is collinear with z'".

Figure 2A:
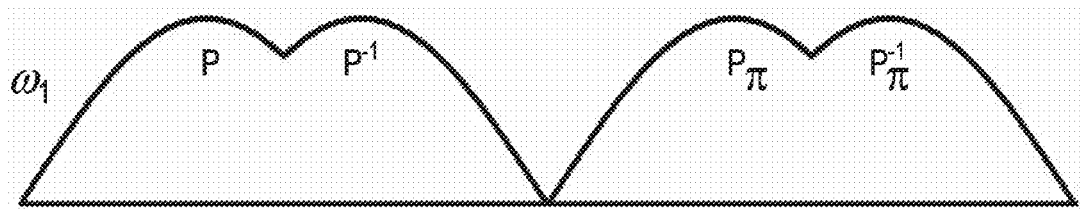
FIG. 2A illustrates amplitude and phase modulation functions of an SC pulse used for RAFF.

Consider the motion of a magnetization vector in the $\omega_{eff}$-frame, starting with M initially along the z" axis as shown in FIG. 2A. In this case, M evolves around the axis of a cone which is defined by E and the angle $\epsilon = \pi/4$. By setting the pulse length to $$T_p = \frac{\pi}{\gamma E}, \tag{9}$$

M will undergo a $\pi$ rotation on the cone, and attains a final orientation along y". This rotation is equivalent to a net rotation of $\pi/2$ in both rotating frames, since y"=y'. Hereafter, the RF modulation functions producing this rotation will be denoted by the operator P.

After accomplishing the first P segment in the time interval $[0, T_p]$, the magnetization is then returned to the z" axis during the interval $[T_p, 2T_p]$ using the inverse pulse, $P^{-1}$. The inverse is created by performing a $\pi$ phase shift and modulating with the functions, $$\omega_1(t) = |\omega_i^{max} \sin(\omega_1^{max} t - (\sqrt{2}+1)\pi)| \text{ for } t = [T_p, 2T_p] \tag{10}$$

and $$\Delta\omega(t) = -\omega_1^{max} \cos(\omega_1^{max} t - (\sqrt{2}+1)\pi) \text{ for } t = [T_p, 2T_p]. \tag{11}$$

To simplify the pulse and for ease of implementation, the FM function can be converted to the equivalent phase modulation (PM) function given by $$\phi(t) = \int_0^t \Delta\omega(t')dt'. \qquad (12)$$

In the AM and PM format, $P^{-1}$ is created by reversing the AM and PM functions of P and then adding $\pi$ to all phases as shown in FIG. 2A.

Figure 2B:
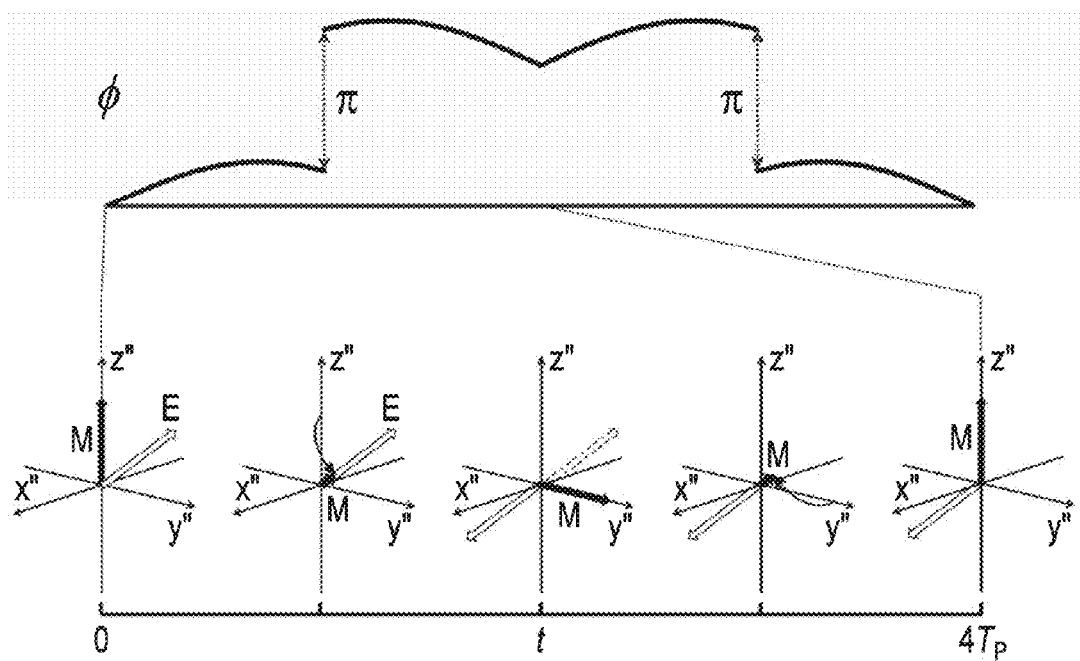
FIG. 2B illustrates the evolution of M during portions of the SC pulse.

FIG. 2A illustrates the amplitude and phase modulation functions of the SC pulse used for RAFF. The $\pi$ phase shift between P and $P^{-1}$ (and between $P_\pi$ and $P_\pi^{-1}$) leads to rotation of M from y" back to z". FIG. 2B shows the evolution of M during the P and $P^{-1}$ portions of the pulse. The phase modulation is obtained by integrating frequency modulation functions given by Eqs. (8 and 11) over four times pulse duration given by Eq. (9) to fulfill condition $B_{eff}(t)=|\gamma^{-1} d\alpha/dt|$.

Part 3

Figure 3A:
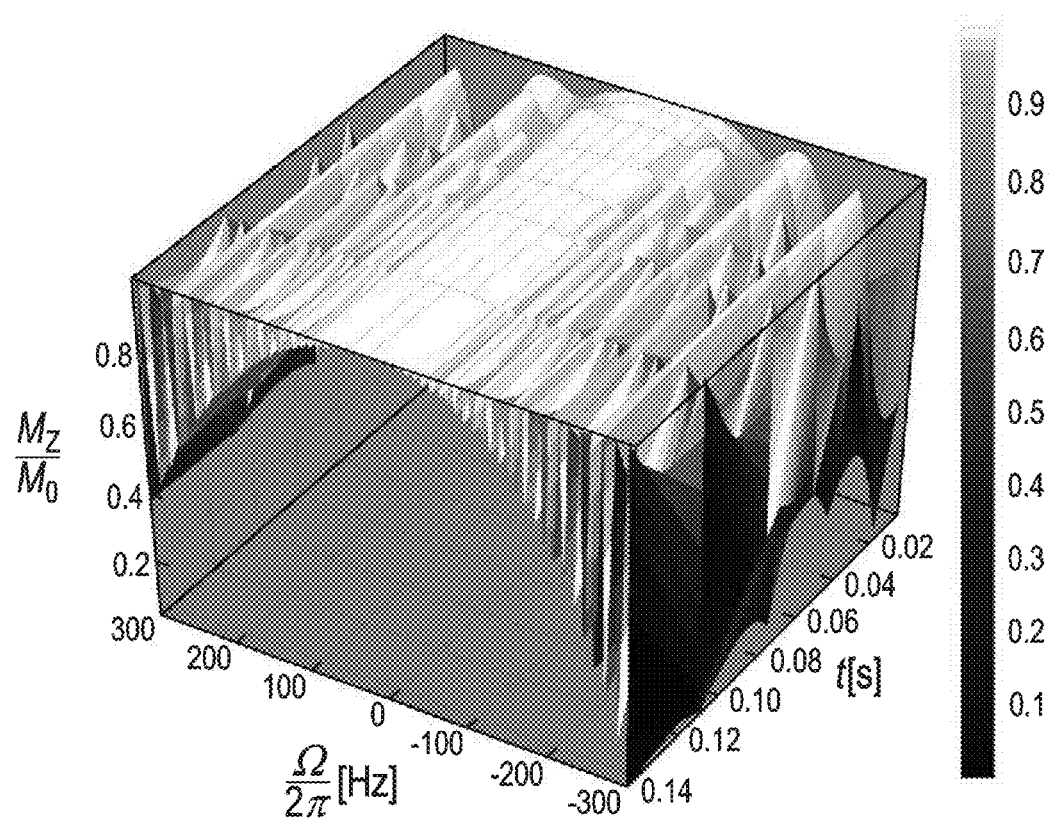
FIG. 3A illustrates a z-axis magnetization profile of the SC pulse as a function of pulse train time duration.
Figure 3B:
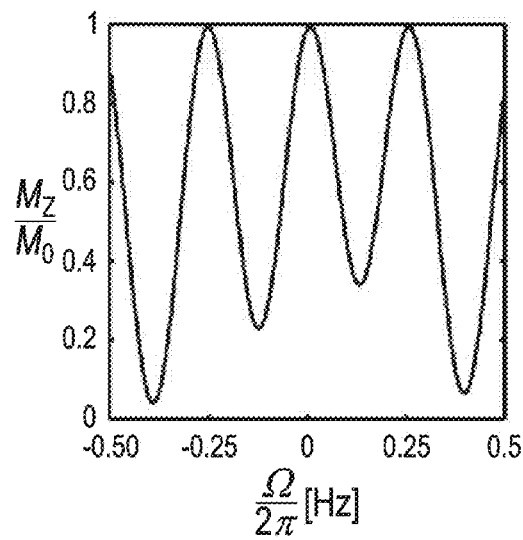
FIGS. 3B-3E illustrate selected pulse train time durations.
Figure 3C:
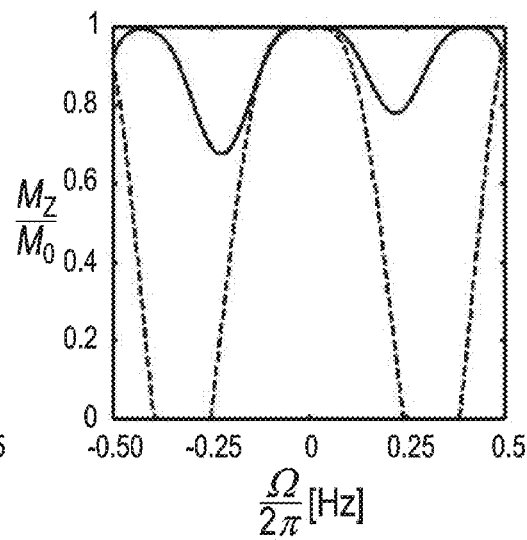
Figure 3D:
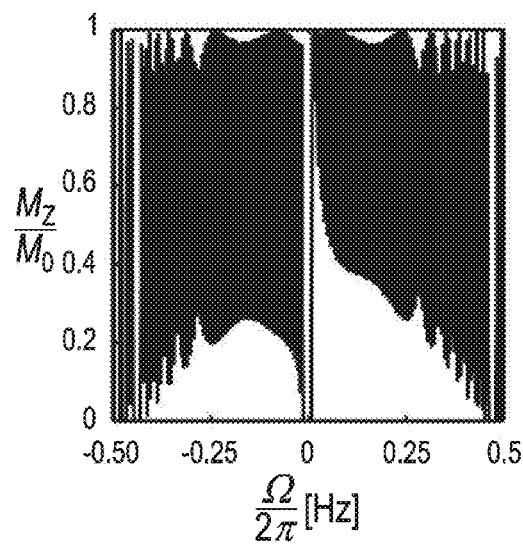
Figure 3E:
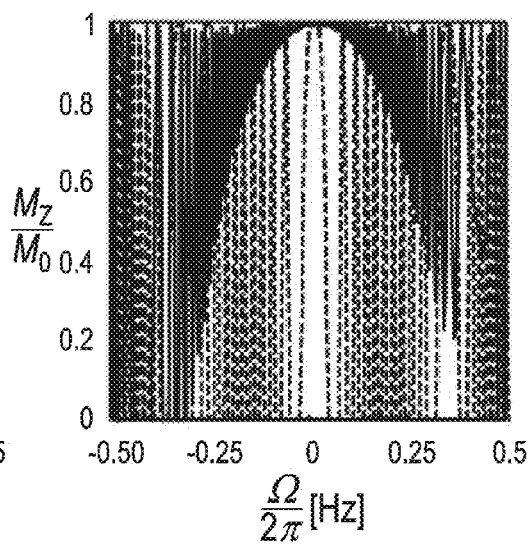

The composite SC pulse is driven by the AM and FM functions given by the Eqs. (7-8, 10-11) and the length of each P segment is given by Eq. (9). The (P) portion corresponds to the pulse during the time interval $[0,T_p]$ and $(P^{-1})$ portion corresponds to the SC pulse during the pulse time duration $[T_p,2T_p]$, as shown in FIG. 2. The $P^{-1}$ is inverse of P, formed by reversing the AM and PM functions and adding $\pi$ phase shift. The utilization of $P^{-1}$ compensates for the artifacts that arise from $B_1$ inhomogeneities. During the course of this composite pulse $PP^{-1}$, magnetization arrives first to the y" axis and then returns back to the +z" following an opposite trajectory as shown in FIG. 2. If the same lobes are used in the pulse (i.e, PP instead of $PP^{-1}$), M undergoes $2\pi$ rotation around the E-field. To compensate for frequency offset artifacts and obtain reasonable pulse profile with long pulse trains, the $P_\pi P_\pi^{-1}$ is introduced after $PP^{-1}$ producing $PP^{-1}P_\pi P_\pi^{-1}$ composite pulse. The $P_\pi$ and $P_\pi^{-1}$ are formed from P and $P^1$, respectively by adding a $\pi$ phase shift. The structure of SC $PP^{-1}P_\pi P_\pi^{-1}$ composite pulse follows BIR4 design and provides sufficient refocusing properties ($B_1$ and $\Omega$) for pulse lengths as shown in FIG. 3A. The pulse profiles of the $PP^{-1}P_\pi P_\pi^{-1}$ pulses as shown in FIG. 3C and FIG. 3E indicate improved refocusing property as compared to the $PP^{-1}PP^{-1}$ with no $\pi$ phase shift as shown in FIG. 3B and FIG. 3D. When the $PP^{-1}P_\pi P_\pi^{-1}$ pulse profile was compared to the profile of the hard $\pi$ pulse train, a wider profile is achieved with SC pulse as shown in FIG. 3C and FIG. 3E.

FIG. 3A illustrates a z-axis magnetization profile of the SC pulse as a function of pulse train time duration. The $PP^{-1}PP^{-1}$ with the 4.53 ms pulse train time duration (as shown in FIG. 3B) and 144.82 ms (as shown in FIG. 3D) are compared to the $PP^{-1}P_\pi P_\pi^{-1}$ with the same durations, respectively (FIGS. 3C and 3E). The dashed lines in FIG. 3C and FIG. 3E are pulse train profiles for 8 and 256 hard $\pi$ pulses with power $\omega_1^{max}/(2\pi)=625$ Hz evenly spaced between 0 and 4.53 in (FIG. 3C) and 0 and 144.82 ms in (FIG. 3E). The simulations were carried out with 8 pulse train time durations (FIG. 3A) and 500 off-resonance fragments (FIGS. 3A-E) using Bloch equations.

Figure 4:
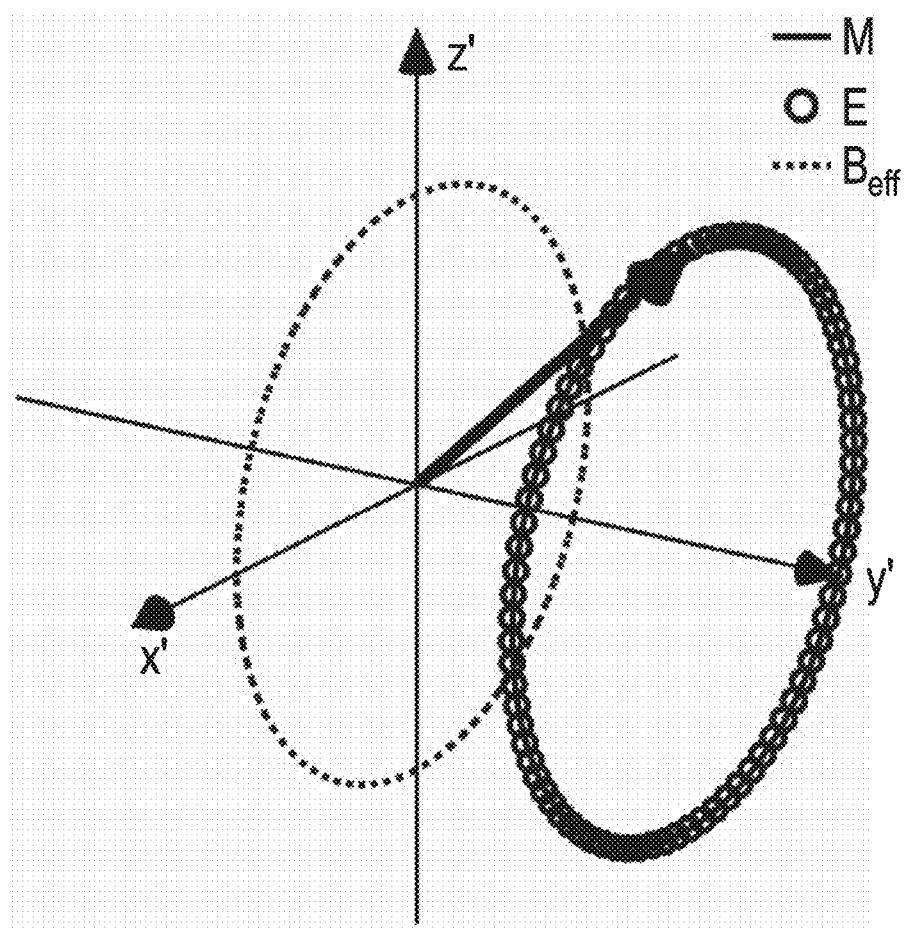
FIG. 4 illustrates magnetization (M) trajectory, E field, and $B_{eff}$ during an SC pulse in the $\omega_{RF}$-frame.

The fictitious field E acts as a locking field. This can be shown by performing Bloch simulations when placing M along the E field ($M_0=[0, 2^{-1/2}, 2^{-1/2}]$) and applying continuously SC pulse according to Eqs. (7 and 8). As shown in FIG. 4, the magnetization vector is locked along the E field during the application of the SC pulse. This demonstrates that the fictitious field E is a locking field.

FIG. 4 illustrates magnetization (M) trajectory (solid line), E field (o) and $B_{eff}$ (dotted line) during SC pulse in the $\omega_{RF}$-frame. The evolution of initial M along E field (thick arrow) is calculated using Bloch simulator during one sine/cosine period with the parameters: $\omega_1^{max}/(2\pi)=625$ Hz, 500 points during the length of one cycle of duration 1.6 ms. The relaxations during the SC pulses are ignored in the figure. E field ($=\gamma^{-1}[\omega_1, d\alpha/dt, \Delta\omega]$) is plotted in every $6^{th}$ point of the pulse. For comparison, the $B_{eff}(=\gamma^{-1}[\omega_1, 0, \Delta\omega])$ is presented in the figure.

Part 4

Next, consider the dipolar relaxations between two identical isolated spins. A description of the relaxations during frequency modulated pulses entails consideration of the time-dependence of the relaxation functions. The Wigner rotation matrices can be used to transform between the various frames of interest with the following substitutions $$\alpha \to \alpha(t)$$

$$\omega_{eff} \to \omega_{eff}(t) \qquad (13)$$

These transformations can be used to describe relaxations during adiabatic hyperbolic secant (HS) family pulses. In the current work, for the calculation of the relaxation functions during RAFF, an additional transformation to the fictitious frame of reference E is used, which is performed by rotating $\omega_{eff}$-frame by the angle $\epsilon(t)$ (which is generally time-dependent).

The relaxation rate constants in the E-frame can be obtained using spectral density functions written in the laboratory frame (LF) and transformed first to the $\omega_{eff}$-frame and then to the fictitious frame of reference, E using Wigner rotating matrixes. The time-dependent spectral densities in this case are written in the frame rotating triply at $\omega_0$, $\omega_{eff}(t)$ and E(t). The expansion for the dipolar Hamiltonian in the $\omega_{eff}$-frame is written as $$H_{dd}(t)^* = \sum_{m=-2}^{m=2} F_{2m}(t) A_{2m}^* \qquad (14)$$

Here $F_{2m}(t)$ is a time-dependent stochastic function that models the interaction of the spin system with its environment and $A^*_{2m}$ is a second rank irreducible spherical tensor transformed to the $\omega_{eff}$-frame. From standard methods from angular momentum theory, $$A_{2m}^* = \sum_{m'=-2}^{2} A_{2m'} D_{m',m}^{(2)}(-\psi(t), -\alpha(t), -\omega t], \qquad (15)$$

where the $D_{m',m}^{(2)}$ are the second rank Wigner rotation matrices that are used to transform the second rank tensors from the LF to the $\omega_{eff}$-frame and $\Psi$ is the angle evolved around $\omega_{eff}$.

$$\psi(t) = \int_{t_0}^t \omega_{eff}(\zeta)d\zeta. \qquad (16)$$

The second rank Wigner rotation matrix element is $$D_{m',m}^{(2)}(-\Psi(t),-\alpha(t),-\omega t)=e^{im'\Psi(t)}d_{m',m}^{(2)}(-\alpha(t))e^{im\alpha}. \qquad (17)$$

The $d_{m',m}^j(-\alpha(t))$ (here j=2) is second rank reduced Wigner matrix element given by $$d_{m',m}^j(-\alpha(t)) = \sqrt{(j+m)!(j-m)!(j+m')!(j-m')!} \times \qquad (18)$$

-continued $$\sum_{l} \frac{(-1)^l}{(j-m'-l)!(j+m-l)!(l+m'-m)!l!}$$

$$(\cos(\alpha(t)/2)^{2j+m-m'-2l}(-\sin(\alpha(t)/2)^{m'-m+2l}$$

where the sum is over the values of the integer l for which the factorial arguments are greater or equal to zero. For RAFF relaxations, an additional transformation to the E-frame is performed by the angle $\epsilon$ (note that $\epsilon$ is time-independent for the SC pulse, defined by Eqs. 7 and 8) leading to expressions for the relaxation rate constants in the E-frame $$T_{1\rho,E}^{-1} = \qquad (19)$$

$$\frac{3}{40} \hbar^2 \gamma^4 r^{-6} \sum_{q=-2}^{2} \sum_{q_1=-2}^{2} \sum_{q_2=-2}^{2} 2 \frac{\tau_c}{1+(\tau_c(q\omega_0+\omega_{\mathit{eff}}(t)+q_2\omega_E(t))^2}$$

$$\ldots \times \sum_{m'm} d_{m'm}^{(2)}(\alpha(t)) \sum_{m'm} d_{m'm}^{(2)}(\varepsilon) q_2^2$$

$$T_{2\rho,E}^{-1} = \qquad (20)$$

$$\frac{3}{80} \hbar^2 \gamma^4 r^{-6} \sum_{q=-2}^{2} \sum_{q_1=-2}^{2} \sum_{q_2=-2}^{2} 2 \frac{\tau_c}{1+(\tau_c(q\omega_0+q_1\omega_{\mathit{eff}}(t)+q_2\omega_E(t))^2}$$

$$\ldots \times \sum_{m'm} d_{m'm}^{(2)}(\alpha(t)) \sum_{m'm} d_{m'm}^{(2)}(\varepsilon)(q_2+2)(3-q_2).$$

Here $\omega_E = \gamma E$. In FIG. 5, the comparison between the sensitivity of RAFF and adiabatic $T_{1\rho}$ and $T_{2\rho}$ to the change of correlation time is presented. The calculations were performed for the isolated two spins ½ undergoing dipolar interactions. The figure illustrates the sensitivity of the rate constants obtained with RAFF to the change of the correlation times. Since the on-resonance CW spin-lock $R_{1\rho} = R_2$, the largest change of the rate constants as a function of the correlation times occurs. With RAFF, the $R_{1\rho,E}$ is close in the sensitivity of CW $R_{1\rho}$. An intriguing property of RAFF found by the theoretical calculations is that $R_{1\rho,E} = R_{2\rho,E}$ (FIG. 5). The validity of the model was tested by the transformation of the relaxation functions obtained in the E-frame back to the laboratory frame to obtain $R_1$ and $R_2$ using Kronecker δ-functions.

Figure 5A:
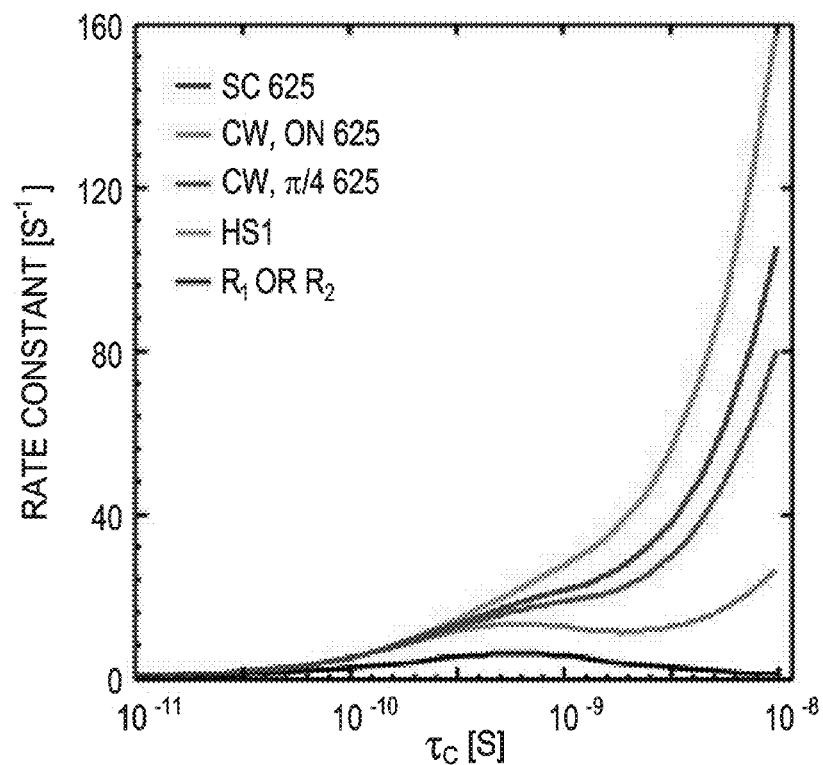
FIGS. 5A and 5B illustrate calculated longitudinal and transverse relaxation rate constants, respectively.
Figure 5B:
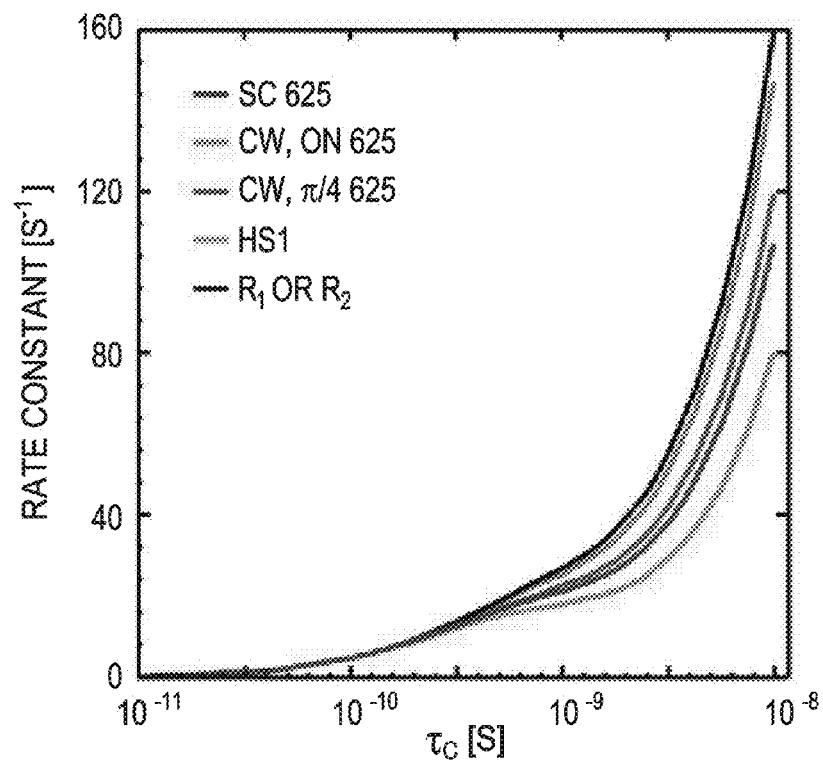

FIG. 5 illustrates calculated longitudinal (FIG. 5A) and transverse (FIG. 5B) relaxation rate constants. In FIG. 5A, the on-resonance $R_{1\rho}$, off-resonance $R_{1\rho}$ with angle π/4, and $R_{1\rho,E}$ are presented. In FIG. 5B, on-resonance $R_{2\rho}$, off-resonance $R_{2\rho}$ with the angle π/4, and $R_{2\rho,E}$. The $R_{1\rho,E}$ and $R_{2\rho,E}$ are calculated using Eqs. (7, 8, 19, 20). The on- and off-resonance $R_{1\rho}$ and $R_{2\rho}$ are generated $\omega_1^{max}/(2\pi)=625$ Hz. The adiabatic $R_{1\rho}$ and $R_{2\rho}$ curves (HS1) are calculated using pulse modulation functions and equations for relaxation rate constants. The $R_1$ and $R_2$ curves are calculated using a particular model.

Part 5
Subpart A

Phantom experiments can be carried out using a 40-cm-bore 4.7 T magnet (OMT, Inc., Oxon, UK) with Varian $^{UNI}$-$_{TY}$INOVA console (Varian Inc., Palo Alto, Calif.). RF power can be transmitted and received using a custom-built linearly-polarized surface coil. To assess dipolar relaxation, measurements can be performed on the methyl protons of acetate (chemical shift=1.9 ppm) in a glycerol/water solution (ratio 0.9/0.1 by weight). Glycerol (99.9% grade) can be used as received (Fischer Scientific Inc., USA), and the sodium acetate (Sigma-Aldrich Inc., USA) can have 100 mM. The signal intensity (SI) decays can be measured using SC pulses with the peak power $\omega_1^{max}/(2\pi)=625$ Hz by increasing the number of $PP^{-1}P_\pi P_\pi^{-1}$ segments. The total numbers of the SC segments can be 2, 4, 8, 16, 24, 32, 40 and 64 or 2, 16, 32, 48 and 64 leading to pulse train time durations from 4.53 to 144.82 ms with $T_p \approx 0.565$ ms. Adiabatic $T_{1\rho}$ and $T_{2\rho}$ measurements can be performed with HS pulses. For the adiabatic $T_{1\rho}$ measurements the train of AFP pulses can be placed prior to the adiabatic half passage (AHP). For the $T_{2\rho}$ measurements the train of AFP pulses can be placed after the AHP pulse prior to the localization by adiabatic selective refocusing (LASER) used for the voxel (4×4-6×4-6 mm³) selection. The pulse trains can include the variable number of pulses (4, 8, 16, 20, 24, 28 and 32 pulses) with the peak power $\omega_1^{max}/(2\pi)=3.5$ kHz and $T_p=3.2$ ms. Repetition time TR=5 s can be used. Steady state contribution can be investigated by performing SI decay measurements when magnetization is oriented initially along +z, 60°, 90° (in yz plane) and then inverted along −z in 5 mM Gd-DTPA (Magnevist, Berlex Laboratories, Wayne, N.J.) in water. Initial flips can be performed using BIR4 pulses ($T_p=6$ ms, adiabaticity factor R=200, $\omega_1^{max}/(2\pi)=3.5$ kHz) with corresponding flip angles and inversion of M performed using HS pulse ($T_p=6$ ms, adiabaticity factor R=10, $\omega_1^{max}/(2\pi)=3.5$ kHz) prior to SC or adiabatic pulse trains.

For comparison with RAFF, conventional on- and off-resonance $T_{1\rho}$ measurements can be conducted at 4.7 T magnetic field, using adiabatic spin-lock pulse in ethanol (>99.5% Sigma-Aldrich Inc., USA) mixed with water with volume fractions 0.5/0.5. The adiabatic spin-lock pulse can include an adiabatic half passage (AHP) pulse followed by continuous wave (CW) spin-lock. The magnetization M can be excited to $\alpha=\pi/2$ and $\alpha=\pi/4$ for the on- and off-resonance experiments, respectively, and locked at these angles by the CW portion of the adiabatic spin-lock pulse. After spin-lock, magnetization can be returned back to z axis using reverse AHP pulse. For the relaxation measurements the spin-lock time duration can be incremented at the constant power $\omega_1^{max}/(2\pi)=625$ kHz.

Subpart B

Human experiments can be performed using healthy volunteers (n=5). The MRI system can include a Varian $^{UNITY}$I-NOVA console (Varian Inc., Palo Alto, Calif., USA) interfaced to a 90 cm bore 4 T magnet (OMT, Inc., Oxon, UK). A volume coil based on a TEM design can be used for RF transmission and reception. After global shimming, 11 transversal slices can be acquired using fast spin echo $T_2$-weighted imaging (TR=4.5 s, matrix=256×128, FOV=20×20 cm², echo train length=8, with echo spacing=15 ms, slice thickness=3 mm) pulse sequence. SI decay curves can be measured with RAFF, $T_{1\rho}$, and $T_{2\rho}$ preparation from two slices separately using TurboFLASH imaging readout (TR=10 ms and echo time TE=5 ms). TR between segments can be 5 s, number of segments=4, number of excitation NEX=4, matrix=256×256, FOV=20×20 cm², slice thickness=3 mm One slice can be selected in the plane of striatum. To measure human brain maps with RAFF, the SC pulses can be applied in the same manner as in phantom studies ($\omega_1^{max}/(2\pi)=625$ Hz, $T_p=0.565$ ms, number of blocks=2, 16, 32, 48 and 64). For adiabatic $T_{1\rho}$ and $T_{2\rho}$ measurements, the HS pulses ($T_p=6$ ms, R=10, $\omega_1^{max}/(2\pi)\approx 1300$ Hz, number of pulses in the pulse trains=4, 8, 12, and 16) can be used. The power calibration can be performed in each human experiment using hard pulse prior to the LASER spectroscopic localization matching the voxel position and size with the midbrain area. For the $T_1$ mapping 6 images can be collected by using adiabatic inversion (HS1, R=10, $T_p$=6 ms) pulse placed prior to the TurboFLASH imaging readout and varying inversion time (6 values evenly spaced between 0.3 and 1.4 s). To evaluate SS contribution, the same inversion pulse can be used prior to the SC pulse train to obtain relaxation measurement with M starting from −z. Free-precession $T_2$s can be measured using adiabatic double-spin echo pulse sequence and by varying the time intervals between two AFP pulses. For $T_2$ measurements, the echo times can be varied between 12 and 128 ms. $B_1$ maps can be measured from two volunteers to ensure $B_1$ homogeneity within the area of the deep brain structures. The $B_1$ maps can be generated from 20 images collected by applying hard pulse and varying the pulse time duration. The pulse time duration can be evenly changed between 0.1 and 0.8 ms. The RF energy deposited by the RAFF and AFP pulse trains increased with pulse train durations, and can be kept below the FDA limit for the longest pulse trains. The estimation of 3 kg tissue load of the coil can be used in the calculation. The SAR values can be below the guidelines of 3 W/kg averaged over the head for 10 min (http://www.fda.gov/cdrh/ode/mri340.pdf). Computed SAR values may be in good agreement with the hardware SAR monitor of the system. The total scan time can be approximately 60 minutes per subject.

Part 6

SI decay curves, measured starting with M from −z and +z, can be simultaneously fitted using non-linear fitting with least square cost function using exponential decay and recovery to the steady state $$S_{+z}=S_{0,+z}e^{-Rt}-S_{SS}(1-e^{-R_{SS}t})$$

$$S_{-z}=S_{0,-z}e^{-Rt}-S_{SS}(1-e^{-R_{SS}t}) \quad (21)$$

Here $S_0$ is initial signal intensity, R relaxation rate constant of the signal decay, $S_{SS}$ is the SS signal intensity for $t \to \infty$ and $R_{SS}$ is the rate constant of the recovery to the SS. The dimensionless SS is defined here by SS=$S_{SS}/S_0$. Note, the same formalism can be applied for the estimation of the longitudinal free-precession relaxations in rapid pulsed MR. The relaxation maps can be generated using pixel-by-pixel analysis with the model described by Eq. (21). The comparison can be performed with the maps generated using single mono-exponential function for decay of M from +z. Regions of interests (ROIs) can be outlined for globus pallidus, putamen and caudate nuclei. Relaxation time constants can be determined from these ROIs and average values calculated. All values are presented in mean ±standard deviation.

Part 7

Figure 6:
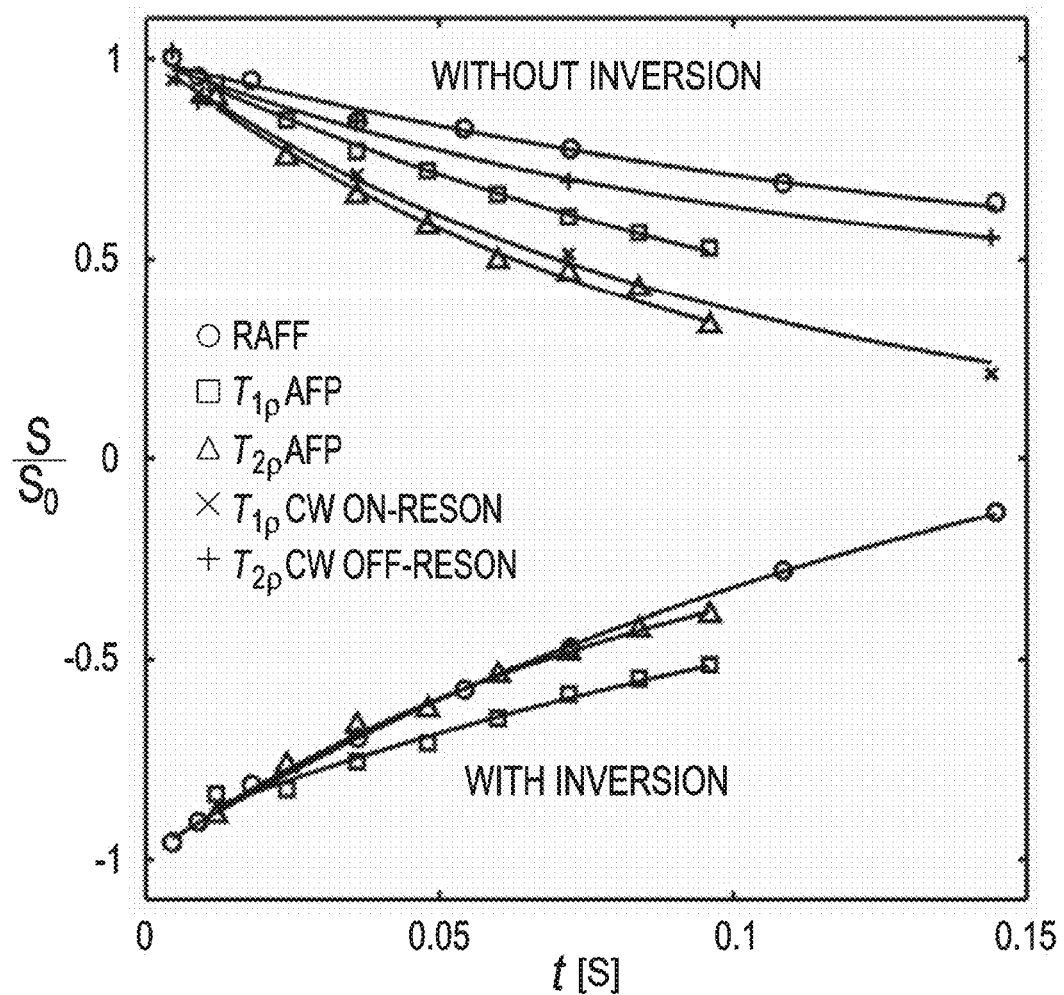
FIG. 6 illustrates signal intensity decay curves using RAFF pulse, adiabatic $T_{1\rho}$, $T_{2\rho}$, continuous wave $T_{1\rho}$ and continuous wave off-resonance $T_{1\rho}$.

The relaxation measurements of acetate (—CH₃ resonance at 1.9 ppm) dissolved in glycerol/water mixture (g/w) can be performed to probe a system undergoing dipolar relaxations. FIG. 6 illustrates a comparison between SI decay curves measured with RAFF and $T_{1\rho}$ and $T_{2\rho}$ techniques. In this figure the results using acetate in glycerol/water solution with the ratio 0.9/0.1 are shown. The viscosity of solution was $\eta \approx 220$ cp. The signal recovery after the inversion pulse illustrates the formation of the SS with RAFF, but not with adiabatic $T_{1\rho}$ and $T_{2\rho}$. The results of the analysis using Eq. 22 (FIG. 6) by setting R=$R_{SS}$ shows comparable rate constants with RAFF and adiabatic $T_{1\rho}$ ($R_{RAFF}$=6.6 s⁻¹, $R_{1\rho}$=6.5 s⁻¹).

FIG. 6 illustrates SI decay curves of the acetate (100 mM) dissolved in glycerol/water (0.9/0.1) mixture measured with RAFF pulse (circles $\omega_1^{max}/(2\pi)$=625 Hz), adiabatic $T_{1\rho}$ (squares), $T_{2\rho}$ (triangles), continuous wave $T_{1\rho,(x,\omega_1^{max}/(2\pi))}$=625 Hz) and continuous wave off-resonance $T_{1\rho}$. (+, $\omega_1^{max}/(2\pi)$=625 Hz, $\Delta\omega/(2\pi)$=625 Hz). Two independent acquisitions are presented for RAFF and adiabatic techniques. In the top portion of the figure, M was not perturbed prior to the SC pulses, and in the bottom portion, M was inverted prior to the SC pulses. Relaxation curves (solid lines) can be fitted using Eq. (21).

Figure 7:
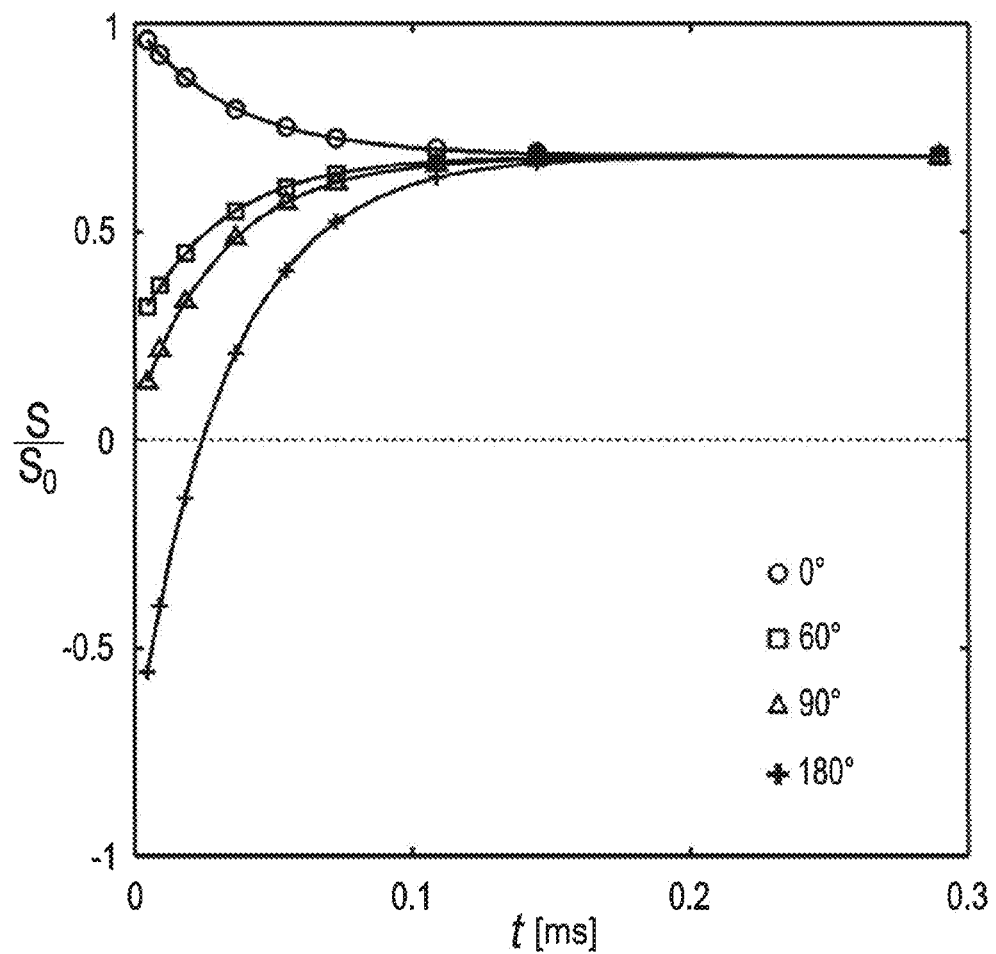
FIG. 7 illustrates normalized signal intensity decay curves obtained with RAFF in 5 mM Gd-DTPA deionized aqueous solution.

Similar rate constants can be found with adiabatic $T_{2\rho}$ and on- and off-resonance $T_{1\rho}$ ($R_{2\rho}$=10.5 s⁻¹, $R_{1\rho,on}$=9.9 s⁻¹ and $R_{1\rho,off}$=10.0 s⁻¹). The SS 0.4 can be found for RAFF which is in the same range as off-resonance $T_{1\rho}$ (SS=0.42). No SS was obtained using adiabatic relaxation methods (SS=−0.03—0.04). There is no SS formation for the on-resonance $T_{1\rho}$. Therefore, a two parameter mono-exponential function can be used for the fitting of the on-resonance $T_{1\rho}$. The SS formation during RAFF is shown in FIG. 7 where several initial flip angles can be used to show that M evolves to the same equilibrium magnetization. This shows that the relaxation rate constants are independent of the initial flip angle, suggesting that the homogenous excitation is unnecessary.

To evaluate the RAFF method, the dependence of the relaxation rate constants of water/ethanol mixture on the power of the SC pulses and the offset from the carrier frequency can be investigated and compared with the off-resonance spin-lock $T_{1\rho}$. The contour plots which compare the relaxation rate constants' dependencies on $\Delta\omega$ and $\omega_1^{max}/(2\pi)$ are shown in FIG. 7. It can be seen that RAFF can provide more uniform distribution of the rate constants within the range of $\Delta\omega \pm 50$ Hz as compared to spin-lock $T_{1\rho}$. On the other hand, the dependence of rate constants on power measured with RAFF can be greater as compared to off-resonance spin-lock $T_{1\rho}$.

FIG. 7 illustrates normalized SI decay curves obtained with RAFF in 5 mM Gd-DTPA deionized aqueous solution. Magnetization is placed initially to the different angles (0°, 60°, 90° and 180°) relatively to the z' axis prior to the application of the SC pulse trains. In the figure, the solid line represents fitting to the experimental data (circles) using Eq. (21) for either $S_{+z}$ (0° flip) or $S_{-z}$ (60°, 90° and 180° flips). The relaxation rate constants and the SS are independent of the initial angle between M and z'. The results are normalized to the fitted $S_0$ obtained from the 0° experiment. In the present sample, R=30.7±1.4 (mean±sd) and SS=0.684±0.001. Magnetization can be excited to the 60° and 90° by using BIR-4 pulse ($T_p$=6 ms, $\omega_1^{max}/(2\pi)$=3.5 kHz) and 180° by HS1 ($T_p$=6 ms, $\omega_1^{max}/(2\pi)$=3.5 kHz). Note, that the additional SC pulse train of duration 289.64 ms was added to better observe SS formation.

Part 8

In vivo MRI contrast can be based on the rotating frame relaxations in the E-frame using RAFF in the human brain at 4 T. RAFF can be compared with $T_1$ and $T_2$, and with adiabatic $T_{1\rho}$ and $T_{2\rho}$ contrasts from a human brain slice (FIG. 8). The relaxation time constant values obtained using RAFF in the mid brain areas can be larger than the $T_2$ and $T_{2\rho}$ and smaller than the $T_1$ and $T_{1\rho}$ as shown in Table 1. The RAFF method can provide substantially different (p<0.001, paired Student's t-test) relaxation time constants as compared to adiabatic $T_{1\rho}$ and $T_{2\rho}$ as well to $T_1$ and $T_2$ Table 1 illustrates a comparison of the RAFF relaxation time constants with, $T_1$ and $T_2$, adiabatic $T_{1\rho}$ and $T_{2\rho}$ in representative midbrain areas of normal human brain at 4 T (n=5).

Figure 8A:
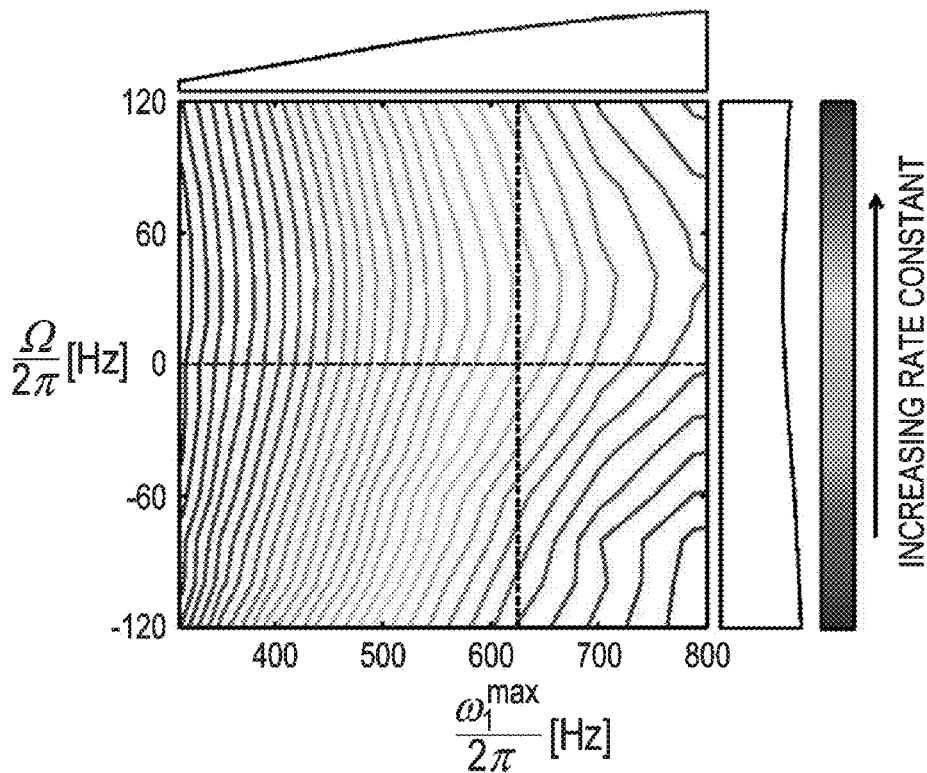
FIGS. 8A and 8B illustrate two-dimensional contour plots of the rate constants of ethanol/water mixture as a function of offset frequency of the pulses and pulse amplitude measured with RAFF pulse train and off-resonance spin-lock $T_{1\rho}$.
Figure 8B:
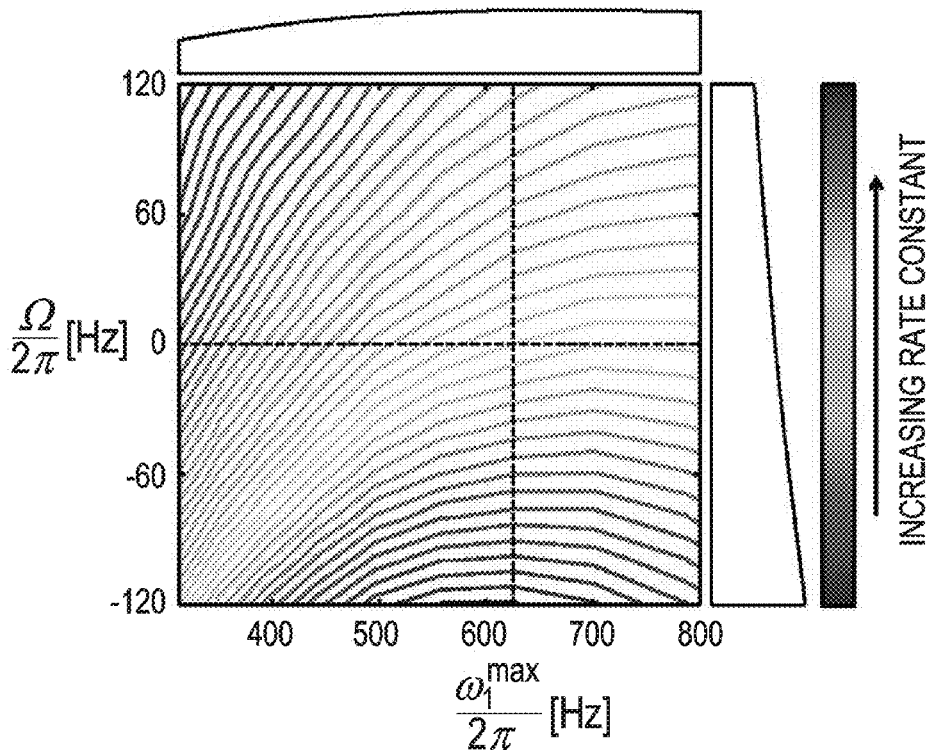

FIG. 8 illustrates two-dimensional contour plots of the rate constants of ethanol/water mixture as a function of offset frequency of the pulses and pulse amplitude ($\omega_1^{max}/(2\pi)$) measured with 5 RAFF pulse train durations (FIG. 8A) and off-resonance spin-lock $T_{1\rho}$ (FIG. 8B). The contour lines designate 2.5% change in the measured relaxation rate constants from the nominal values measured with $\omega_1^{max}/$ $(2\pi)=625$ Hz. The rate constants measured with $\omega_1^{max}/(2\pi)=625$ Hz and $\Delta\omega=0$ were $R_{RAFF}=5.3$ s$^{-1}$ and $T_{1\rho,off}R=3.9$ s$^{-1}$. The horizontal and vertical profiles from the dashed lines are presented on the top and left side of the contour plots, respectively. Fittings for both methods are performed using the model given by Eq. (21).

TABLE 1

|  | $T_1$ [ms] | $T_{1p}$ [ms] | $T_{RAFF}$ [ms] | $T_{2p}$ [ms] | $T_2$ [ms] |
|---|---|---|---|---|---|
| GP | 1045.4 ± 42.2 | 161.3 ± 2.8 | 105.4 ± 2.2 | 55.4 ± 3.1 | 46.5 ± 1.8 |
| P | 1324.9 ± 37.5 | 189.2 ± 3.4 | 126.8 ± 3.1 | 65.7 ± 1.9 | 51.4 ± 3.2 |
| CN | 1420.5 ± 48.2 | 221 ± 8.1 | 134.8 ± 3.1 | 76.6 ± 3 | 64.8 ± 2.1 |

A comparison in the contrast to noise (CNR) ratio measured with RAFF versus $T_{1\rho}$, $T_{2\rho}$, $T_1$ and $T_2$ is summarized in Table 2.

Table 2 illustrates a comparison of contrast to noise ratios (CNR) between RAFF, adiabatic $T_{1\rho}$ and $T_{2\rho}$ in different brain areas in the human brain at 4 T (n=5). In the table, GP denotes globulus pallidus, P denotes putamen and CN denotes caudate nuclei.

TABLE 2

|  | CNR $T_1$ [%] | CNR $T_{1\rho}$ [%] | CNR $T_{RAFF}$ [%] | CNR $T_{2\rho}$ [%] | CNR $T_2$ [%] |
|---|---|---|---|---|---|
| GP vs. P | 21.1 ± 2.3 | 14.7 ± 1.8 | 16.8 ± 2.1 | 15.8 ± 4.3 | 9.4 ± 4.2 |
| GP vs. CN | 26.4 ± 2.1 | 26.9 ± 2.5 | 21.8 ± 2.3 | 27.6 ± 5.7 | 28.2 ± 3.3 |
| P vs. CN | 6.7 ± 0.7 | 14.3 ± 3.5 | 5.8 ± 4.0 | 14.0 ± 4.6 | 20.7 ± 5.0 |

The RAFF CNR can be comparable with the CNR provided by adiabatic $T_{1\rho}$ and $T_{2\rho}$. This allows obtaining the rotating frame relaxation contrast in the mid brain areas with lower power than required by adiabatic pulse sequences. Results from human brain suggest that the exchange relaxation pathway may be a significant contributor to in vivo MRI contrast observed with RAFF, since $T_{RAFF}$ is shorter than that of obtained with adiabatic $T_{1\rho}$. Additionally, the contribution of the SS Eq. (21) can be considered. Since, the contribution of different relaxation mechanisms to $T_{RAFF}$ and SS remain unknown, R and $R_{SS}$ in Eq. (21) can be independent fitting parameters in the relaxation map analysis. Specifically, the RAFF relaxation time constants in the human brain tissue analyzed using Eq. (21) may be ≈20% smaller than the relaxation time constants obtained from the same images using single mono-exponential decay function (FIG. 9). The fractional SS map (FIG. 9B) represents the contribution of the SS to the RAFF and displays the spatial variation of the SS in the mid brain areas. Due to distribution of the SS in the human brain slice generated by RAFF, the SS contribution may improve the detected contrast between the different areas.

FIG. 9 illustrates representative relaxation maps from human brain obtained using $T_1$ (FIG. 9A), adiabatic $T_{1\rho}$ (FIG. 9B), RAFF (FIG. 9C), adiabatic $T_{2\rho}$ (FIG. 9D) and $T_2$ (FIG. 9E) relaxation mapping techniques.

FIG. 10A illustrates a map of the time constant describing relaxation along a fictitious field ($T_{RAFF}$), analyzed using Eq. (13). FIG. 10B illustrates a map of the fractional steady state obtained from the same fitting and then normalized by the initial signal intensity: $SS=S_{SS}/S_0$. FIG. 10C illustrates a map of $T_{RAFF}$ generated using only a single mono-exponential function.

The lower power requirement of RAFF is an advantage of this technique as compared to adiabatic $T_{1\rho}$ and $T_{2\rho}$ methods. The average power delivered in the brain tissue during adiabatic $T_{1\rho}$, $T_{2\rho}$ and RAFF acquisitions can be 1.07 W/kg, 1.48 W/kg and 1.10 W/kg, respectively. Because the longest pulse train duration of RAFF can be 1.5 times longer as compared to the adiabatic $T_{1\rho}$, the averaged power depositions can be similar The delivered energy per unit time for RAFF can be 83% and 63% of the energies of the adiabatic $T_{1\rho}$, $T_{2\rho}$, respectively. Comparison between SC pulse and the on-resonance CW pulse (used for the spin-lock) with the equal peak powers and pulse durations leads to the 61% of the SAR of RAFF versus CW spin-lock.

Part 9

Relaxations along fictitious field (RAFF) can be used to generate contrast. The rotating frame relaxation contrast can be generated in vivo using frequency swept pulses under sub-adiabatic condition. This can lead to a locking field in the fictitious frame of reference, the E-frame. Analytically, the $T_{\rho,E}$ and $T_{2\rho,E}$ influenced by dipolar relaxations are identical during RAFF. The RAFF method can be advantageous for human brain mapping with sufficiently low RF power as compared to adiabatic $T_{1\rho}$ and $T_{2\rho}$. Low RF power deposition and the peak power during RAFF with the property of initial flip of M independent relaxation may yield applicability for human relaxation mapping studies at high magnetic fields.

A variety of different frames of reference can be used with the present subject matter and a doubly-tilted, doubly rotating frame is an example. Other examples include multiply tilted frames of reference. In various examples, relaxation in a lower order frame of reference is used to determine relaxation in a higher order frame of reference. For example, one method includes creating contrast by detecting spin relaxation along a fictitious field in a higher order rotating frame where the fictitious field is comprised of magnetic field components that arise due to modulating the effective field in a lower order rotating frame.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
a signal generator configured to couple with a magnetic resonance transmitter coil; and
a processor configured to execute instructions to control the signal generator, the instructions including forming a sequence of waveforms, the sequence configured to generate spin relaxation in a fictitious field in a third rotating frame of reference based on at least one magnetic field component that arises based on an effective field in a second rotating frame of reference relative to a first rotating frame of reference, wherein the third rotating frame of reference is of a higher order than the second rotating frame of reference and the second rotating frame of reference is of a higher order than the first rotating frame of reference.

2. The system of claim 1 wherein the processor is configured to modulate the effective field.

3. The system of claim 1 wherein the processor is configured to maintain the effective field at a constant value.

4. The system of claim 1 wherein the fictitious field includes a swept frequency.

5. The system of claim 1 wherein the fictitious field arises under sub-adiabatic conditions.

6. The system of claim 1 wherein the fictitious field includes an axis of quantization of the third rotating frame of reference.

7. The system of claim 1 further including:
a receiving coil configured to detect the relaxation in the fictitious field; and
an output device coupled to the receiving coil and wherein the output device is configured to render human perceivable data.

8. A method comprising:
directing a plurality of waveforms to a region of interest, the plurality of waveforms configured to produce a fictitious field vector; and
generating data based on a magnetic resonance signal received from the region, the data corresponding to relaxation of magnetization in a third rotating frame and based on relaxation arising in a second rotating frame, wherein the fictitious field vector arises in the third rotating frame, the third rotating frame having a Z-axis collinear with the fictitious field vector and wherein a Z-axis of the second rotating frame is collinear with $\omega_{eff}$, wherein $\omega_{eff}$ is a vector based on a frequency offset and based on an amplitude of a pulse of the plurality of waveforms.

9. The method of claim 8 wherein the plurality of waveforms is configured to modulate the fictitious field vector as a function of time.

10. The method of claim 8 wherein the relaxation of magnetization in the second rotating frame is based on a combination of longitudinal rotating frame relaxation and transverse rotating frame relaxation of the second rotating frame.

11. The method of claim 8 wherein directing the plurality of waveforms includes sequentially applying a first pulse train and an excitation pulse.

12. The method of claim 11 wherein the first pulse train is applied before the excitation pulse.

13. The method of claim 11 wherein the first pulse train is applied after the excitation pulse.

14. The method of claim 8 wherein directing the plurality of waveforms includes applying a pulse having sine and cosine functions with equal amplitude.

15. The method of claim 8 wherein $\omega_{eff}$ is a vector sum of a frequency offset and an amplitude.

16. The method of claim 8 wherein rotation of the magnetization from the Z-axis of the second rotating frame to an X-Y plane of the second rotating frame causes the magnetization to precess about a cone having an angle relative to the fictitious field of approximately 45 degrees during the pulse.

17. The method of claim 8 wherein directing the plurality of waveforms includes applying a waveform having a plurality of lobes, each lobe having a first segment and a second segment, wherein the first segment includes a sine modulation function and cosine modulation function and the second segment includes a backward first segment.

18. The method of claim 17 wherein the first segment has phase zero and the second segment has phase 180 degrees.

19. The method of claim 17 wherein the plurality of waveforms includes a sequence of four segments wherein a first segment includes sine amplitude modulation and cosine frequency modulation, a second segment includes amplitude and phase of the first segment driven backwards and a 180 degree shifted phase and a third segment includes a 180 degree shifted phase of the first segment and a fourth segment includes a 180 degree shifted phase of the second segment.

20. The method of claim 19 wherein a relaxation rate of magnetization of dipolar origin during a duration of the pulse is slower than the relaxation in the second rotating frame.

21. The method of claim 19 wherein the pulse causes refocusing of magnetization.

22. The method of claim 11 wherein the relaxation includes a combination of transverse relaxation in the third rotating frame and of longitudinal relaxation in the third rotating frame.

23. The method of claim 13 wherein the relaxation includes a combination of transverse relaxation in the third rotating frame and of longitudinal relaxation in the third rotating frame.

24. The method of claim 13 wherein the relaxation includes transverse relaxation orthogonal to the fictitious field in the third rotating frame.

25. The method of claim 8 wherein generating data includes fitting measured signal intensity decay to an exponential function.

26. The method of claim 25 wherein fitting measured signal intensity decay to the exponential function includes fitting to function having a plurality of exponentials.

27. The method of claim 8 wherein generating data includes establishing a steady state.

\* \* \* \* \*

UNITED STATES PATENT AND TRADEMARK OFFICE
CERTIFICATE OF CORRECTION

PATENT NO. : 7,932,719 B2
APPLICATION NO. : 12/731936
DATED : April 26, 2011
INVENTOR(S) : Timo Liimatainen et al.

It is certified that error appears in the above-identified patent and that said Letters Patent is hereby corrected as shown below:

In column 2, line 66, delete "views" and insert -- views. --, therefor.

In column 4, line 9, delete "frequency, a" and insert -- frequency, --, therefor.

In column 5, line 26, delete "pulse" and insert -- pulse. --, therefor.

In column 5, line 48, delete "$\alpha_{eff}$-frame" and insert -- $\omega_{eff}$-frame --, therefor.

In column 6, line 20, delete "manner" and insert -- manner. --, therefor.

In column 6, line 25, delete "$E=\sqrt{\sqrt{2}\omega_1}^{max}$," and insert -- $E=\sqrt{2}\ \omega_1^{max}$ --, therefor.

In column 9, line 8, delete "1" and insert -- I --, therefor.

In column 9, lines 63-64, delete "$^{UNI}_{TY}$INOVA" and insert -- $^{UNITY}$INOVA --, therefor.

In column 10, line 59, delete "mm" and insert -- mm. --, therefor.

In column 11, line 35, delete "$S_{-z}=S_{0,-z}e^{-Rt}-S_{ss}(1-e^{-Rss t})$" and insert -- $S_{-z}=S_{0,-z}e^{-Rt}-S_{ss}\left(1-e^{-Rss t}\right)$ --, therefor.

In column 11, line 66, delete "$T_{1p}$," and insert -- $T_{1p}$. --, therefor.

In column 12, line 54, delete "$T_1$" and insert -- $T_{1p}$ --, therefor.

In column 14, line 4, delete "similar" and insert -- similar. --, therefor.

In column 14, line 16, delete "$T_{p,E}$" and insert -- $T_{1p,E}$ --, therefor.

Signed and Sealed this
Twenty-seventh Day of September, 2011

David J. Kappos
*Director of the United States Patent and Trademark Office*